United States Patent
Stewart et al.

(10) Patent No.: US 6,754,593 B1
(45) Date of Patent: Jun. 22, 2004

(54) METHOD AND APPARATUS FOR MEASURING DEFECTS

(75) Inventors: Edward C. Stewart, Buda, TX (US); Jason A. Grover, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 61 days.

(21) Appl. No.: 10/163,566

(22) Filed: Jun. 6, 2002

(51) Int. Cl.[7] .................................................. G06K 9/00
(52) U.S. Cl. ........................... 702/35; 702/81; 382/149; 348/129
(58) Field of Search .............................. 700/109, 110, 700/121, 212; 382/149; 348/129; 356/349; 702/35, 81, 82, 83, 84; 438/10, 12, 18

(56) References Cited

U.S. PATENT DOCUMENTS

| | | | | |
|---|---|---|---|---|
| 5,991,699 A | * | 11/1999 | Kulkarni et al. | 702/83 |
| 6,104,835 A | * | 8/2000 | Han | 382/225 |
| 6,222,936 B1 | * | 4/2001 | Phan et al. | 382/149 |

* cited by examiner

*Primary Examiner*—Kamini Shah
(74) *Attorney, Agent, or Firm*—Williams, Morgan & Amerson

(57) ABSTRACT

A method for measuring defects includes receiving a defect characteristic measurement for each measurement site in a first subset of a plurality of measurement sites on a workpiece. A second subset of the plurality of measurement sites is defined. The size of the second subset is based on the defect characteristic measurements of the first subset of the plurality of measurement sites. A metrology tool is directed to measure the defect characteristic at each of the measurement site in the second subset responsive to the size of the second subset being greater than zero. A system includes a metrology tool and a controller. The metrology tool is configured to measure a defect characteristic at each of a first plurality of measurement sites on a workpiece. The controller is configured to compare the measured defect characteristics at the first plurality of measurement sites against a first predetermined threshold and direct the metrology tool to measure the defect characteristic at each of a second plurality of measurement sites on the workpiece responsive to the measured defect characteristics being greater than the first predetermined threshold.

36 Claims, 4 Drawing Sheets

METHOD AND APPARATUS FOR MEASURING DEFECTS

BACKGROUND OF THE INVENTION

1. Field of the Invention

This invention relates generally to the field of semiconductor device manufacturing and, more particularly, to a method and apparatus for measuring defects.

2. Description of the Related Art

There is a constant drive within the semiconductor industry to increase the quality, an reliability and throughput of integrated circuit devices, e.g., microprocessors, memory devices, and the like. This drive is fueled by consumer demands for higher quality computers and electronic devices that operate more reliably. These demands have resulted in a continual improvement in the manufacture of semiconductor devices, e.g., transistors, as well as in the manufacture of integrated circuit devices incorporating such transistors. Additionally, reducing the defects in the manufacture of the components of a typical transistor also lowers the overall cost per transistor as well as the cost of integrated circuit devices incorporating such transistors.

Generally, a set of processing steps is performed on a lot of wafers using a variety of processing tools, including photolithography steppers, etch tools, deposition tools, polishing tools, rapid thermal processing tools, implantation tools, etc. The technologies underlying semiconductor processing tools have attracted increased attention over the last several years, resulting in substantial refinements. However, despite the advances made in this area, many of the processing tools that are currently commercially available suffer certain deficiencies. In particular, such tools often lack advanced process data monitoring capabilities, such as the ability to provide historical parametric data in a user-friendly format, as well as event logging, real-time graphical display of both current processing parameters and the processing parameters of the entire run, and remote, ie., local site and worldwide, monitoring. These deficiencies can engender non-optimal control of critical processing parameters, such as throughput, accuracy, stability and repeatability, processing temperatures, mechanical tool parameters, and the like. This variability manifests itself as within-run disparities, run-to-run disparities and tool-to-tool disparities that can propagate into deviations in product quality and performance, whereas an ideal monitoring and diagnostics system for such tools would provide a means of monitoring this variability, as well as providing means for optimizing control of critical parameters.

One technique for improving the operation of a semiconductor processing line includes using a factory wide control system to automatically control the operation of the various processing tools. The manufacturing tools communicate with a manufacturing framework or a network of processing modules. Each manufacturing tool is generally connected to an equipment interface. The equipment interface is connected to a machine interface that facilitates communications between the manufacturing tool and the manufacturing framework. The machine interface can generally be part of an advanced process control (APC) system. The APC system initiates a control script based upon a manufacturing model, which can be a software program that automatically retrieves the data needed to execute a manufacturing process. Often, semiconductor devices are staged through multiple manufacturing tools for multiple processes, generating data relating to the quality of the processed semiconductor devices.

Data gathered during the course of wafer processing is used to identify and attempt to mitigate the effects of process and equipment variations by implementing automatic control techniques and/or automatic fault detection and classification (FDC) techniques based on the collected metrology data. Current semiconductor processing techniques typically collect metrology data at a fixed rate (e.g., every fourth lot processed in a tool) or by pre-assigning a fixed percentage of lots for measurement. Because lots are not typically processed in a particular order, the percentage technique sometimes results in periods where multiple lots are measured consecutively, followed by periods where no lots are measured. Such static sampling plans sometimes do not diagnose process or system issues expeditiously. As a result, defective wafers could be manufactured, necessitating costly re-work or scrapping of the wafers.

Different processes performed during the fabrication of devices, by nature, have different propensities for inducing defects in the processed devices. Typically, one process tool may be used to perform a process using different operating recipes (e.g., different etching recipes for different process layers formed on a wafer). Static sampling plans typically measure a predetermined number of wafers processed in the process tool. Such static sampling plans sometimes fail to provide adequate data for effective process control or fault detection given the different defect characteristics of the processes being performed.

The present invention is directed to overcoming, or at least reducing the effects of, one or more of the problems set forth above.

SUMMARY OF THE INVENTION

One aspect of the present invention is seen in a method for measuring defects. The method includes receiving a defect characteristic measurement for each measurement site in a first subset of a plurality of measurement sites on a workpiece. A second subset of the plurality of measurement sites is defined. The size of the second subset is based on the defect characteristic measurements of the first subset of the plurality of measurement sites. A metrology tool is directed to measure the defect characteristic at each of the measurement site in the second subset responsive to the size of the second subset being greater than zero.

Another aspect of the present invention is seen in a system including a metrology tool and a controller. The metrology tool is configured to measure a defect characteristic at each of a first plurality of measurement sites on a workpiece. The controller is configured to compare the measured defect characteristics at the first plurality of measurement sites against a first predetermined threshold and direct the metrology tool to measure the defect characteristic at each of a second plurality of measurement sites on the workpiece responsive to the measured defect characteristics being greater than the first predetermined threshold.

BRIEF DESCRIPTION OF THE DRAWINGS

The invention may be understood by reference to the following description taken in conjunction with the accompanying drawings, in which like reference numerals identify like elements, and in which.

Figure 1:
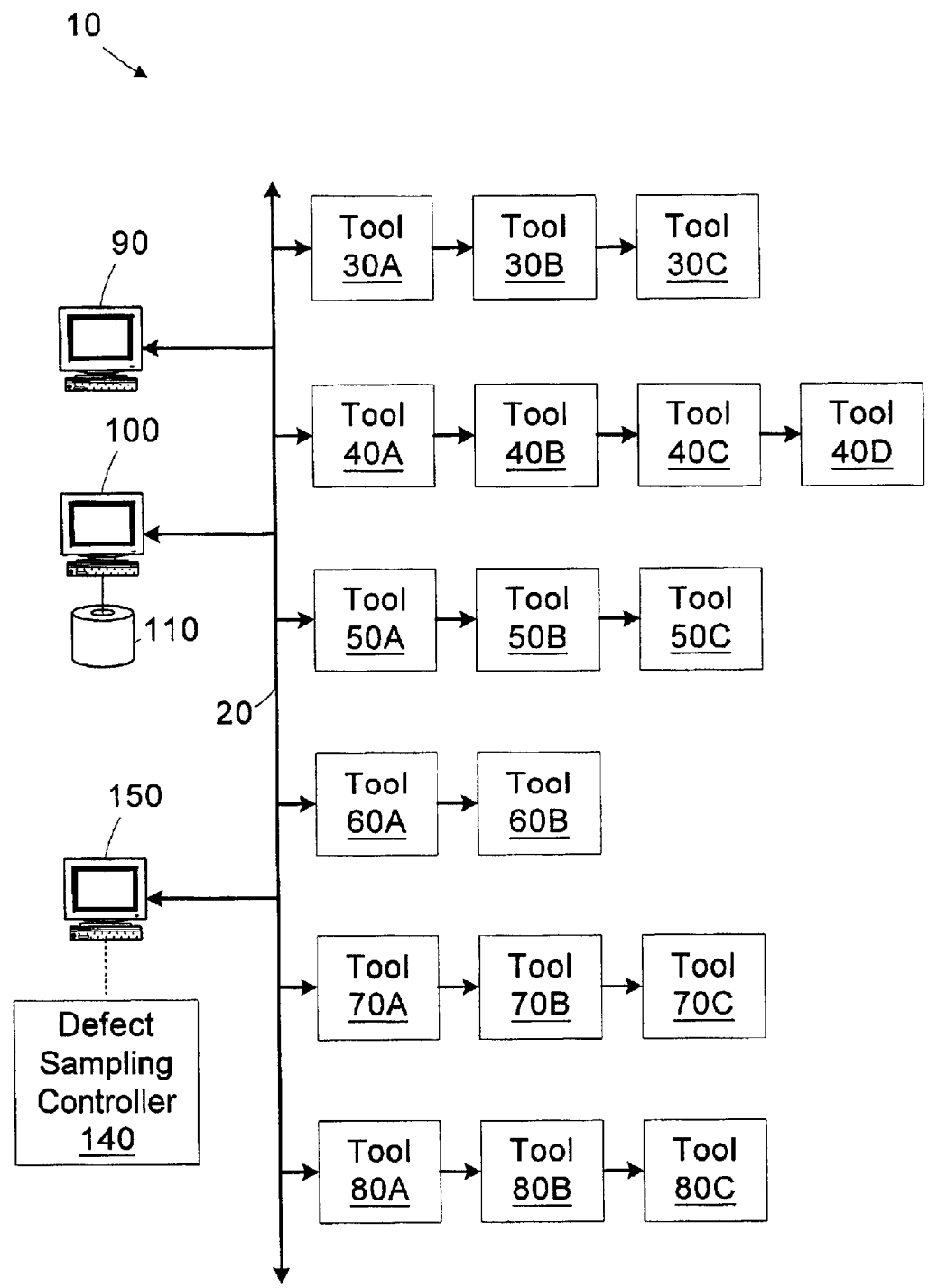
FIG. 1 is a simplified block diagram of a manufacturing system in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Referring to FIG. 1, a simplified block diagram of an illustrative manufacturing system 10 is provided. In the illustrated embodiment, the manufacturing system 10 is adapted to fabricate semiconductor devices. Although the invention is described as it may be implemented in a semiconductor fabrication facility, the invention is not so limited and may be applied to other manufacturing environments. The techniques described herein may be applied to a variety of workpieces or manufactured items, including, but not limited to, microprocessors, memory devices, digital signal processors, application specific integrated circuits (ASICs), or other similar devices. The techniques may also be applied to workpieces or manufactured items other than semiconductor devices.

A network 20 interconnects various components of the manufacturing system 10, allowing them to exchange information. The illustrative manufacturing system 10 includes a plurality of tools 30–80. Each of the tools 30–80 may be coupled to a computer (not shown) for interfacing with the network 20. The tools 30–80 are grouped into sets of like tools, as denoted by lettered suffixes. For example, the set of tools 30A–30C represent tools of a certain type, such as a chemical mechanical planarization tool. A particular wafer or lot of wafers progresses through the tools 30–80 as it is being manufactured, with each tool 30–80 performing a specific function in the process flow. Exemplary processing tools for a semiconductor device fabrication environment include metrology tools, photolithography steppers, etch tools, deposition tools, polishing tools, rapid thermal processing tools, implantation tools, etc. The tools 30–80 are illustrated in a rank and file grouping for illustrative purposes only. In an actual implementation, the tools may be arranged in any physical order or grouping. Additionally, the connections between the tools in a particular grouping are meant to represent only connections to the network 20, rather than interconnections between the tools.

A manufacturing execution system (MES) server 90 directs high level operation of the manufacturing system 10. The MES server 90 monitors the status of the various entities in the manufacturing system 10 (ie., lots, tools 30–80) and controls the flow of articles of manufacture (e.g., lots of semiconductor wafers) through the process flow. A database server 100 is provided for storing data related to the status of the various entities and articles of manufacture in the process flow. The database server 100 may store information in one or more data stores 110. The data may include pre-process and post-process metrology data, tool states, lot priorities, etc.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary information exchange and process control framework suitable for use in the manufacturing system 10 is an Advanced Process Control (APC) framework, such as may be implemented using the Catalyst system offered by KLA-Tencor, Inc. The Catalyst system uses Semiconductor Equipment and Materials International (SEMI) Computer Integrated Manufacturing (CIM) Framework compliant system technologies and is based the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI, which is headquartered in Mountain View, Calif.

The processing and data storage functions are distributed amongst the different computers or workstations in FIG. 1 to provide general independence and central information storage. Of course, different numbers of computers and different arrangements may be used without departing from the spirit and scope of the instant invention.

The manufacturing system 10 also includes a defect sampling controller 140 executing on a workstation 150. As described in greater detail below, the defect sampling controller 140 evaluates the results of defect measurements associated with the tools 30–80 and dynamically adjusts the sampling plans based on the defect measurements. Exemplary measured defects include particle contamination defects, overlay errors, missing or extra patterns, or electrical faults or defects. Although the MES server 90 and defect sampling controller 140 are shown as separate entities, they may be integrated into a single unit. Similarly, the functions of the defect sampling controller 140 described herein may be integrated into a variety of other entities in the manufacturing system 10.

Figure 2:
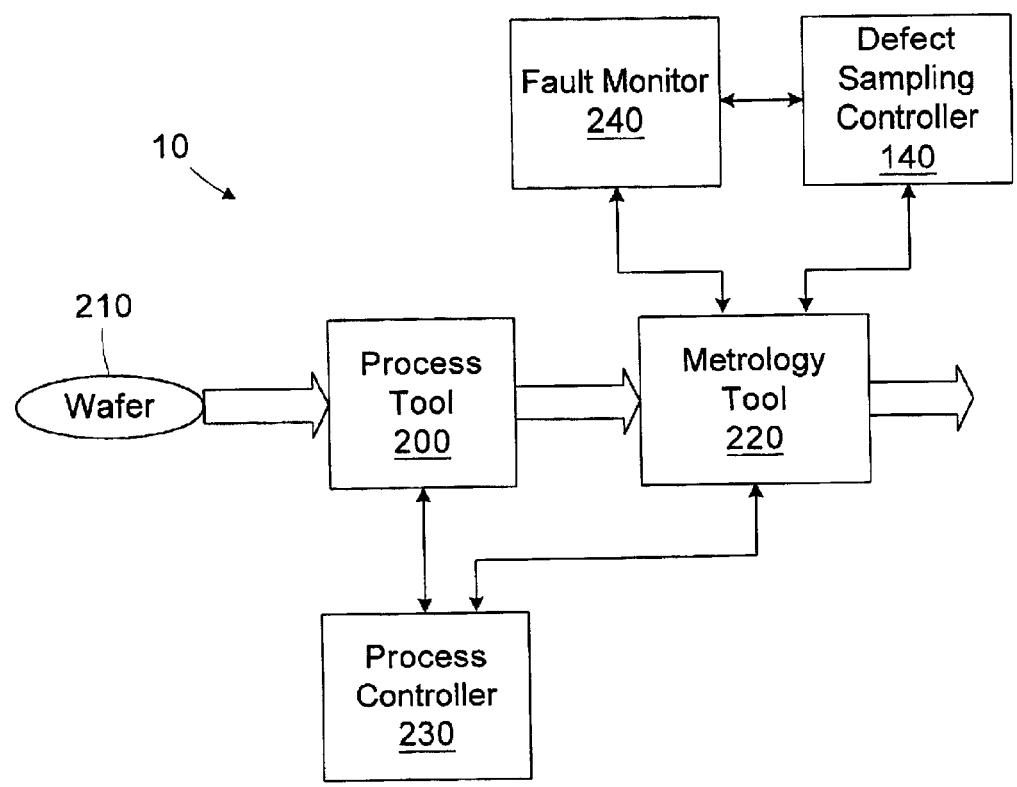
FIG. 2 is a simplified block diagram of a portion of the manufacturing system of FIG. 1.

Referring now to FIG. 2, a simplified block diagram of a portion of the manufacturing system 10 of FIG. 1 is provided. A process tool 200 (e.g., one of the tools 30–80) processes wafers 210 according to one of a plurality of operating recipes. The process tool 200 may also be a single chamber of a multiple chamber tool 30–80. A metrology tool 220 (e.g., one of the tools 30–80) measures defect characteristics of the wafers 210 processed in the process tool 200 to gauge the efficacy of the process implemented by the process tool 200. The metrology data collected by the metrology tool 220 may be passed to a process controller 230 for dynamically updating the operating recipe of the process tool 200 to reduce variation between the measured output characteristic and a target value for the characteristic. The metrology data collected by the metrology tool 200 may also be passed to a fault monitor 240 for fault detection and classification. If the measured output characteristic is outside tolerable limits, the fault monitor 240 may reject the wafer, and the wafer may be reworked or scrapped and/or the process tool 200 may be taken out of service for maintenance.

As described in greater detail below, the defect sampling controller 140 receives defect data from the metrology tool 220 and/or the fault monitor 240, and changes the sampling plan implemented by the metrology tool 220 based on the defect data. The defect sampling controller 140 may process the defect data obtained from the metrology tool 220 directly (i.e., the defect sampling controller 140 may determine if a defect exists), or alternatively, the defect data may be first processed by the fault monitor 240 and the results may be passed to the defect sampling controller 140.

Although the process tool 200, defect sampling controller 140, process controller 230, fault monitor 240, and metrology tool 220 are illustrated as separate units, they may be combined into a single unit or a different number of common units in some embodiments. The particular process performed by the process tool 200 and the particular defect characteristic measured by the metrology tool 220 may vary widely. The instant invention is applicable to a wide variety of process tools 200, which may be related to semiconductor or other types of processing, and the defect characteristic measured by the metrology tool 220 may be selected from a wide range of defect characteristics applicable to the particular product or workpiece being processed or the particular process being performed. For example, the defect characteristic measured by the metrology tool 220 may include physical characteristics, electrical characteristics, or direct defect characteristics. Exemplary parameters include, but are not limited to, process layer thickness, critical dimensions (e.g., line width), across-wafer variation, resistivity, particle defect counts, missing pattern defect counts, extra pattern defect counts, electrical defects, etc.

Figure 3:
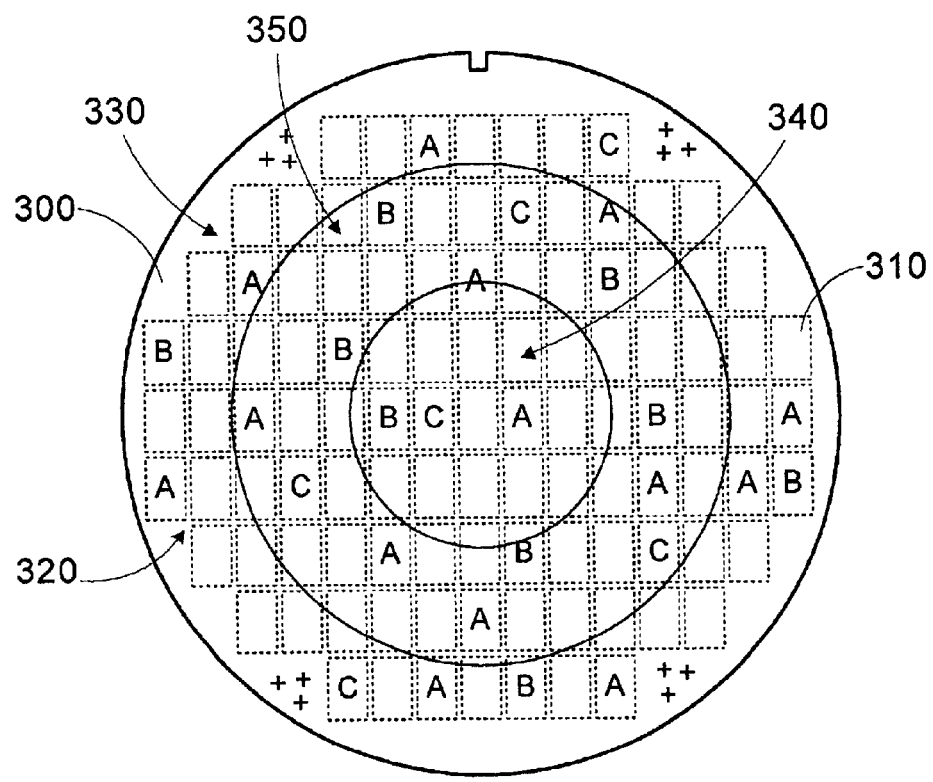
FIG. 3 is a simplified diagram of a semiconductor wafer being processed illustrating a variety of defect measurement sites.

Turning now to FIG. 3, a simplified diagram of a semiconductor wafer 300 being processed is shown. The semiconductor wafer 300 typically includes a plurality of individual semiconductor die 310 arranged in a grid 320. A first set of defect measuring sites, designated by the letter "A" is defined. The metrology tool 220 measures the defect characteristics at each of the sites in the A set. The defect sampling controller 140 evaluates the defect results (i.e., either directly or through an interface with the fault monitor 240). If the defect results meet a predetermined threshold, the defect sampling controller 140 directs the metrology tool 220 to cease measuring. If the defect results do not meet the predetermined threshold, the defect sampling controller 140 directs the metrology tool 220 to continue measuring defect characteristics at additional sites, e.g., the sites designated by the letter "B." In this manner, the defect sampling controller 140 increases the number of measurement sites for the defect measurement so that better fault classification and/or characterization may be performed.

The defect sampling controller 140 analyzes the defect characteristic data after measurement is completed at the "B" sites. The defect sampling controller 140 then compares the results to a second predetermined threshold and terminates measurement if the results are acceptable. If the defect results are not acceptable, the defect sampling controller 140 directs the metrology tool 220 to continue measuring defect characteristics at sites designated by the letter "C." Although three groups of sites are illustrated, this iterative process may continue for any number of groups of measurement'sites.

In one embodiment, the pattern of selection sites for each group A, B, C may be predefined. In another embodiment, the sites within each group A, B, C may be determined randomly. In yet another embodiment, the selection of sites for each group may be selected pseudo-randomly (i.e., random sites within a predefined constraint). For example, x1 sites may be selected from a periphery region 330 near the edge of the wafer, x2 sites from a center region 340, and x3 sites from an intermediate region 350. The invention may be practiced using any variety of site selection techniques. The number of sites in each group may also vary. All groups may have the same number of measurement sites or the numbers may be based on statistical criteria. For example, the number of sites in the first groups (i.e., group "A") should be sufficient to create a statistically significant sample sufficient to determine whether additional testing is warranted. If too few sites are measured, the sample may not adequately predict the defect characteristics of the wafer 300.

Although the invention is illustrated using die locations as defect measurement sites, its application is not so limited. Sites may be selected at different points within a single die area, depending on the nature of the particular defect being measured. The sites could also be designated by X-Y or radial coordinate locations on the wafer independent of the particular locations of the dice 310.

The particular thresholds selected for terminating the measurement activities or increasing the number of measurement sites may vary depending on the particular type of defect being measured. In one illustrative embodiment, the defect sampling controller 140 may determine if X out of Y sites have defect characteristics outside a predetermined range and increase the sample size accordingly. Exemplary defect thresholds include a critical dimension being outside a predetermined range, leakage current or power consumption over a predetermined threshold, particle contamination above a predetermined threshold, layer-to-layer overlay offset outside of a predetermined limit, film thickness measurement one standard deviation over a predetermined threshold, etc. Other relationships may also be used to determine if the number of measurement sites should be increased.

Figure 4:
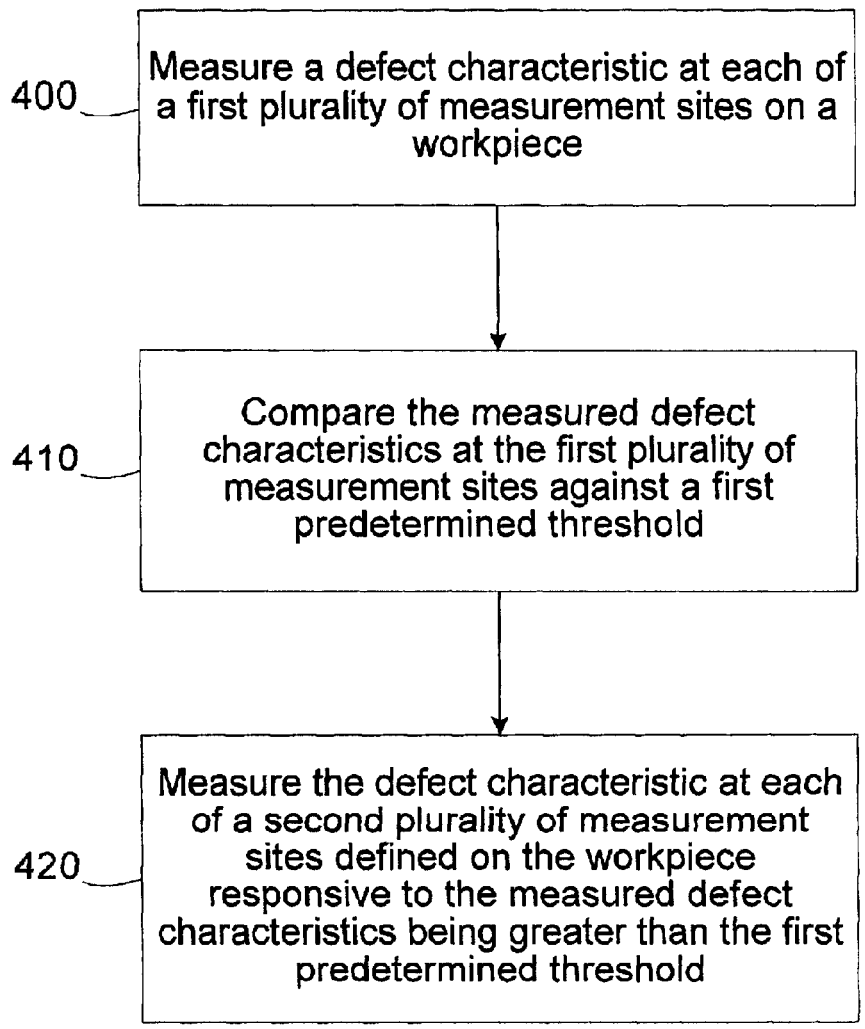
FIG. 4 is a simplified flow diagram of a method for measuring defects in accordance with another illustrative embodiment of the present invention.

Turning now to FIG. 4, a simplified flow diagram of a method for measuring defects in accordance with another illustrative embodiment of the present invention is provided. In block 400, a defect characteristic is measured at each of a first plurality of measurement sites on a workpiece. In block 410, the measured defect characteristics at the first plurality of measurement sites are compared against a first predetermined threshold. In block 420, the defect characteristic is measured at each of a second plurality of measurement sites on the workpiece responsive to the measured defect characteristics being greater than the first predetermined threshold.

Using a dynamic approach to selecting measurement sites, as described herein, provides numerous advantages. First, fault classification and detection effectiveness may be improved because the number of measurement sites can be tailored based on preliminary results to increase the accuracy of the defect characterization. Second, process efficiency is improved because the amount of metrology resources expended may be reduced for wafers that pass the initial defect tests. This reduction increases the throughput of the manufacturing system 10.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
measuring a defect characteristic at each of a first plurality of measurement sites on a workpiece;
comparing the measured defect characteristics at the first plurality of measurement sites against a first predetermined threshold; and
measuring the defect characteristic at each of a second plurality of measurement sites on the workpiece responsive to the measured defect characteristics being greater than the first predetermined threshold.

2. The method of claim 1, further comprising:
comparing at least the measured defect characteristics at the second plurality of measurement sites against a second predetermined threshold; and
measuring the defect characteristic at each of a third plurality of measurement sites defined on the workpiece responsive to the measure defect characteristics at the second plurality of measurement sites being greater than the second predetermined threshold.

3. The method of claim 1, wherein the workpiece comprises a semiconductor wafer and measuring the defect characteristic at each of the first plurality of measurement sites further comprises:
defining a grid of die locations on the semiconductor wafer; and
selecting a first subset of the die locations as the first plurality of measurement sites.

4. The method of claim 3, wherein measuring the defect characteristic at each of the second plurality of measurement sites further comprises select a second subset of the die locations as the second plurality of measurement sites.

5. The method of claim 1, wherein measuring the defect characteristic at each of the first plurality of measurement sites further comprises defining a first plurality of coordinate positions on the workpiece and measuring the defect characteristic at each of the second plurality of measurement sites further comprises defining a second plurality of coordinate positions on the workpiece.

6. The method of claim 1, wherein the workpiece includes at least a first region and a second region and measuring the defect characteristic at each of the first plurality of measurement sites further comprises selecting a first predetermined number of measurement sites in the first plurality of measurement sites from the first region and a second predetermined number of measurement sites in the first plurality of measurement sites from the second region.

7. The method of claim 1, wherein measuring the defect characteristic at each of the first plurality of measurement sites further comprises selecting the first plurality of measurement sites at random positions on the workpiece.

8. The method of claim 1, wherein measuring the defect characteristic further comprises measuring at least one of a physical dimension, an electrical characteristic, a physical defect, and an electrical defect.

9. The method of claim 1, wherein comparing the measurement defect characteristics at the first plurality of measurement site again the first predetermined threshold comprises determining if a predefined proportion of the measurement sites have an associated measurement defect characteristic outside a predetermined range.

10. A method comprising:
receiving a defect characteristic measurement for each measurement site in a first subset of a plurality of measurement sites on a workpiece;
identifying a second subset of the plurality of measurement sites, the size of the second subset being based on the defect characteristic measurement of the first subset of the plurality of measurement sites; and
directing a metrology tool to measure the defect characteristic at each measurement site in the second subset responsive to the size of the second subset being greater than zero.

11. The method of claim 10, further comprising:
receiving the defect characteristic measurement for each measurement site in the second subset of the plurality of measurement sites;
identifying a third subset of the plurality of measurement sites, the size of the third subset being based on the defect characteristic measurements of at least the second subset of the plurality of measurement sites; and
directing a metrology tool to measure the defect characteristic at each measurement site in the third subset responsive to the number of measurement sites in the third subset being greater than zero.

12. The method of claim 10, wherein the workpiece comprises a semiconductor wafer and the method further comprises:
defining a grid of die locations on the semiconductor wafer; and
selecting the die locations as the plurality of measurement sites.

13. The method of claim 10, further comprising defining a plurality of coordinate positions on the workpiece.

14. The method of claim 10, wherein the workpiece includes at least a first region and a second region and the method further comprises selecting a first predetermined number of measurement sites in the first subset from the first region and a second predetermined number of measurement sites in the first subset from the second region.

15. The method of claim 10, further comprising selecting the plurality of measurement sites at random positions on the workpiece.

16. The method of claim 10, wherein receiving the defect characteristic measurements further comprises receiving at least one of a physical dimension measurement, an electrical characteristic measurement, a physical defect measurement, and an electrical defect measurement.

17. The method of claim 10, further comprising determining the size of the second subset based on a proportion of the measurement sites in the first subset having an associated measured defect characteristic outside a predetermined range.

18. A system, comprising:
    a metrology tool configured to measure a defect characteristic at each of a first plurality of measurement sites on a workpiece; and
    a controller configured to compare the measured defect characteristics at the first plurality of measurement sites against a first predetermine threshold and direct the metrology tool to measure the defect characteristic at each of a second plurality of measurement sites on the workpiece responsive to the measured defect characteristics being greater than the first predetermined threshold.

19. The system of claim 18, wherein the controller is further configured to compare at least the measured defect characteristics at the second plurality of measurement sites against a second predetermined threshold and direct the metrology tool to measurement the defect characteristic at each of a the plurality of measurement sites on the workpiece responsive to the measured defect characteristics at the second plurality of measurement sites being greater than the second predetermined threshold.

20. The system of claim 18, wherein the workpiece comprises a semiconductor wafer and controller is further configured to define a grid of die locations on the semiconductor wafer and select a first subset of the die locations as the first plurality of measurement sites.

21. The system of claim 20, wherein the controller is further configured to select a second subset of the die locations as the second plurality of measurement sites.

22. The system of claim 18, wherein the controller is further configured to define a first plurality of coordinate positions on the workpiece as the first plurality of measurements sites and define a second plurality of coordinate positions on the workpiece as the second plurality of measurement sites.

23. The system of claim 18, wherein the workpiece includes at least a first region and a second region and the controller is further configured to select a first predetermined number of measurement sites from the first region and a second predetermined number of measurement sites from the second region as the first plurality of measurement sites.

24. The system of claim 18, wherein the controller is further configured to select the first plurality of measurement sites at random positions on the workpiece.

25. The system of claim 18, wherein the defect characteristic further comprises at least one of a physical dimension, an electrical characteristic, a physical defect, and an electrical defect.

26. The system of claim 18, wherein the controller is further configured to determine if a predetermined proportion of the measurement sites have an associated measured defect characteristic outside a predetermined range.

27. A system, comprising:
    a controller configured receive a defect characteristic measurement for each measurement site in a first subset of a plurality of measurement sites, identify a second subset of the plurality of measurement sites, the size of the second subset being based on the defect characteristic measurement of the first subset of the plurality of measurement sites, and direct a metrology tool to measure the defect characteristic at each measurement site in the second subset responsive to the size of the second subset being greater than zero.

28. The system of claim 27, wherein the controller is further configured to receive the defect characteristic measurement for each of the measurement sites in the second subset, identify a third subset of the plurality of measurement sites the size of the third subset being based on the defect characteristic measurements of at law the second subset of the plurality of measurement sites, and direct the metrology tool to measure the defect characteristic at each measurement site in the third subset of the plurality of measurement sites responsive to the number of measurement sites in the third subset being greater than zero.

29. The system of claim 27, wherein the workpiece comprises a semiconductor wafer and the controller is further configured to defined a grid of die locations on the semiconductor wafer and select the die locations as the plurality of measurement sites.

30. The system of claim 27, wherein the controller is further configured to define a plurality of coordinate positions on the workpiece as the plurality of measurement sites.

31. The system of claim 27, wherein the workpiece includes at least a first region and a second region and the controller is further configured to select a first predetermined number of measurement sites in the first subset from the first region and a second predetermined number of measurement sites in the first subset from the second region.

32. The system of claim 27, wherein the controller is further configured to select the plurality of measurement sites at random positions on the workpiece.

33. The system of claim 27, wherein defect characteristic further comprises measuring at least one of a physical dimension, an electrical characteristic, a physical defect, and an electrical defect.

34. The system of claim 27, wherein the controller is further configured to determine the size of the second subset based on a proportion of the measurement sites in the first subset having an associated measured defect characteristic outside a predetermined range.

35. A system comprising:
    means for measuring a defoot characteristic at each of a first plurality of measurement sites defined on a workpiece;
    means for comparing the measured defect characteristics at the first plurality of measurement sites against a fist predetermined threshold; and
    means for measuring the defect characteristic at each of a second plurality of measurement sites defined on the workpiece responsive to the measured defect characteristics being greater than the first predetermined threshold.

36. A system comprising:
    means for receiving a defect characteristic measurement for each measurement site in a first subset of a plurality of measurement sites on a workpiece;
    means for identifying a second subset of the plurality of measurement sites, the size of the second subset being based on the defect characteristic measurements of the first subset of the plurality of measurement sites; and
    means for directing a metrology tool to an the defect characteristic at each measurement site in the second subset responsive to the size of the second subset being greater than zero.

* * * * *